(12) United States Patent
Wong et al.

(10) Patent No.: US 8,032,218 B2
(45) Date of Patent: Oct. 4, 2011

(54) IMPLANTABLE CARDIAC DEVICE WITH SATELLITE REFRESH

(75) Inventors: Louis Wong, Sunnyvale, CA (US); Dorin Panescu, San Jose, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 519 days.

(21) Appl. No.: 12/183,438

(22) Filed: Jul. 31, 2008

(65) Prior Publication Data
US 2010/0030294 A1   Feb. 4, 2010

(51) Int. Cl.
*A61N 1/362*   (2006.01)
(52) U.S. Cl. .......................................................... 607/30
(58) Field of Classification Search ................ 607/9, 30, 607/37; 128/898, 903, 904
See application file for complete search history.

(56) References Cited

U.S. PATENT DOCUMENTS

| | | |
|---|---|---|
| 6,141,588 A | 10/2000 | Cox |
| 6,402,689 B1 | 6/2002 | Scarantino |
| 6,963,770 B2 | 11/2005 | Scarantino |
| 6,963,771 B2 | 11/2005 | Scarantino |

*Primary Examiner* — Carl H Layno
*Assistant Examiner* — Brian T Gedeon
(74) *Attorney, Agent, or Firm* — Steven M. Mitchell

(57) ABSTRACT

In one embodiment an implantable cardiac device is provided that includes an implantable cardiac stimulation device with an implantable satellite device coupled to it. The implantable satellite device has a charge storage device. The implantable stimulation device having a refresh generator configured to generate a charge and voltage balanced multi-phasic refresh signal with a duration less than a capacitive time constant of an electrode-electrolyte interface of the implantable cardiac device and transmit the charge and voltage balanced multi-phasic refresh signal to the implantable satellite device for charging the charge storage device. In various embodiments, the charge and voltage balanced multi-phasic refresh signal having alternating phase signs and null durations between the alternating phases. In some embodiments, the refresh generator is configured to modulate the multi-phasic waveform refresh signal. The multi-phasic waveform refresh signal may be modulated to contain configuration information, status information, or other information.

37 Claims, 6 Drawing Sheets

IMPLANTABLE CARDIAC DEVICE WITH SATELLITE REFRESH

BACKGROUND

For congestive heart failure, what is important is to have electrodes on the left side ideally in as many locations as possible but there is little room around the epicardial site to place the electrodes. The coronary sinus lead, and branches to some of the veins of the coronary sinus, could carry multiple electrodes on it. But, too many wires passing through the coronary sinus is problematic. So, local integrated circuits or satellite ICs, may be provided to drive the electrodes. The local integrated circuits, however, need power.

If additional wires are used to power the integrated circuits, it increases the number of overall wires going back to the device. As realized by the present inventor, it would be advantageous to use same two existing wires from the device that are used for pacing, to supply the power to the integrated circuits which are handling the electrode.

In this case, each satellite IC may have a capacitor to store the energy. A refresh pulse could be used to charge the capacitor to provide power to the electrode. The refresh is accomplished by delivering an electrical voltage pulse. A refresh pulse may be delivered right after a regular pacing pulse, so it lessens the impact on the sensing operation caused by opening sensing switches, which block sensing during that time. This approach has the disadvantage of requiring continuous pacing. The satellites may loose their configuration if pacing signals do not come at specified times.

For some patients, however, the pacing pulse may not be delivered or needed periodically. In this case, a standalone refresh pulse must be delivered to keep the satellites ICs alive. Although the refresh pulse is a short (e.g. tenths of microseconds) electrical pulse, this is enough to cause excessive disturbance and noise to the regular sensing operation. Therefore, the sensing switches must be opened to block all the noise.

As a result, the sensing operating is being disrupted, turned-off during and after the refresh pulse as well as its recovery, which can be tenths or hundreds of milliseconds. This sensing black-out period can be critical so should be avoided in some applications.

What is needed is to eliminate the need to open and block the sensing switches during and after the refresh pulse. Further, what is needed to allow the sensing system to run continuously—before, during, and after the refresh pulse. Moreover, what is needed is a way to reduce, or preferably eliminate, the sensing black-out period.

SUMMARY

In one implementation, an implantable cardiac device is provided that includes an implantable cardiac stimulation device with an implantable satellite device coupled to it. The implantable satellite device has a charge storage device. The implantable stimulation device having a refresh generator configured to generate a charge and voltage balanced multi-phasic refresh signal with a duration less than a capacitive time constant of an electrode-electrolyte interface of the implantable cardiac device and transmit the charge and voltage balanced multi-phasic refresh signal to the implantable satellite device for charging the charge storage device.

In various embodiments, the charge and voltage balanced multi-phasic refresh signal having alternating phase signs and null durations between the alternating phases.

In some embodiments, the refresh generator is configured to modulate the multi-phasic waveform refresh signal. The modulated the multi-phasic waveform refresh signal may be modulated to contain configuration information, status information, or other information.

In some implementations, a method in an implantable cardiac device for charging a satellite device is provided. The method includes supplying to the satellite device a charge and voltage balanced multi-phasic waveform refresh signal having a duration less than a capacitive time constant of an electrode-electrolyte interface of the implantable cardiac device.

BRIEF DESCRIPTION OF THE DRAWINGS

Further features and advantages of the invention may be more readily understood by reference to the following description taken in conjunction with the accompanying drawings, in which:

FIG. 5 is a plot of a regular negative-positive square wave along with a corresponding voltage plot illustrating the voltage of a capacitor as the regular negative-positive square wave passes through.

FIG. 6 shows a plot of a tri-phasic voltage waveform signal and a corresponding plot illustrating the voltage of a capacitor as tri-phasic voltage waveform signal passes through.

DESCRIPTION

The following description includes the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators will be used to reference like parts or elements throughout.

Overview of Implantable Cardiac Stimulation Device

Figure 1:
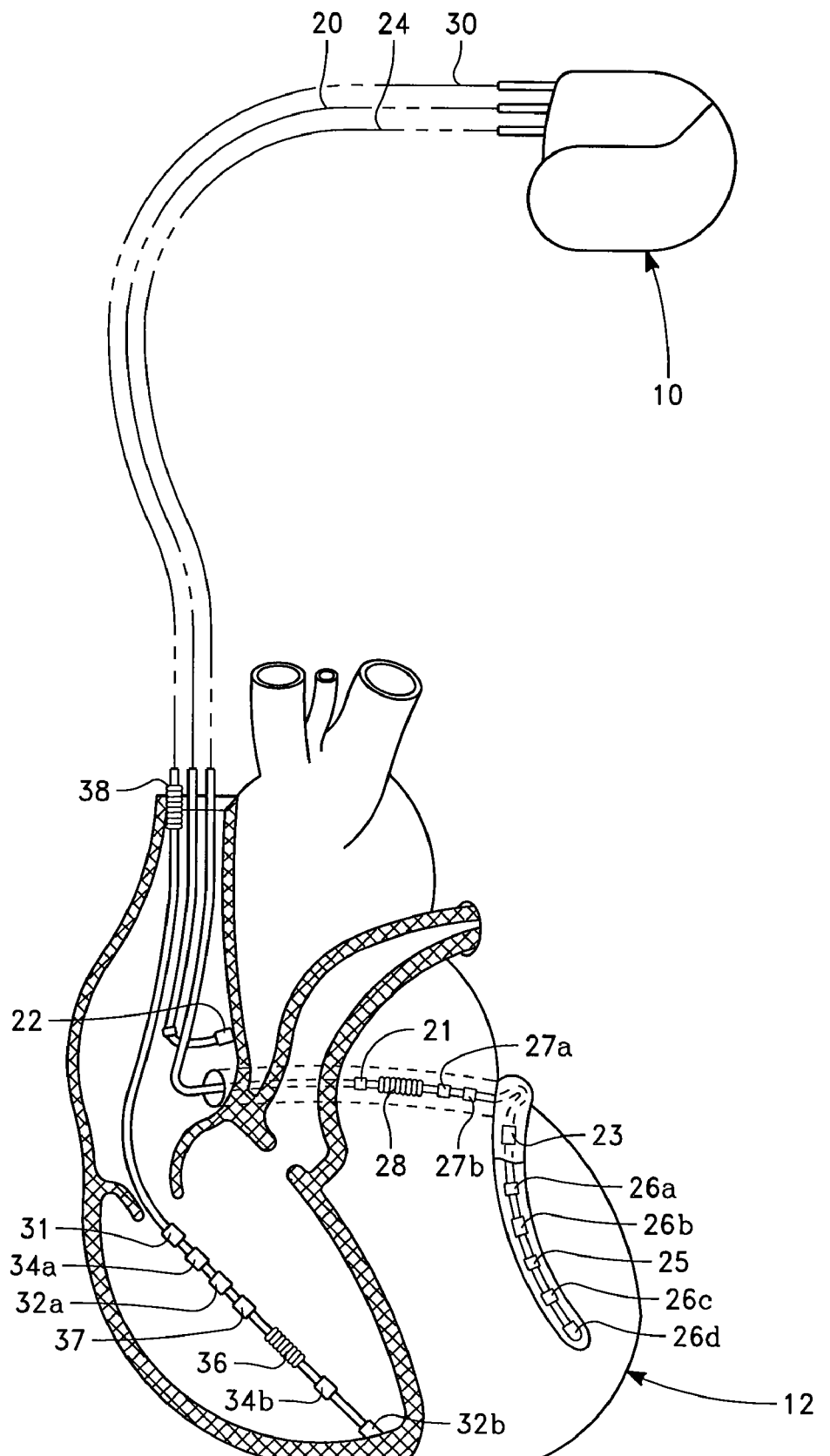
FIG. 1 illustrates a possible embodiment of an implantable cardiac device in electrical communication with a patient's heart.

FIG. 1 illustrates an implantable cardiac stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage, and an atrial ring electrode 23. To sense left atrial and ventricular cardiac signals and to provide left chamber pacing therapy, the stimulation device 10 is coupled to a "coronary sinus" lead 24 designed for placement in the "coronary sinus region" via the coronary sinus or for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, in some embodiments, an exemplary coronary sinus lead 24 is designed to receive atrial and ventricular cardiac signals and to deliver left ventricular pacing therapy.

One or more satellite IC's 21, 23, and 25 may be provided along the coronary sinus lead 24. The satellite IC's 23, and 25 may be controllers used to control sensing and/or pacing using at least a left ventricular tip electrode 26a-26d. The satellite IC 21 may be a controller used to control left atrial senising and/or pacing using at least one of left atrial tip electrodes 27a and/or 27b, and shocking therapy using at least a left atrial coil electrode 28.

The stimulation device 10 is also shown in electrical communication with the patient's heart 12 by way of an implantable right ventricular lead 30 having, in this embodiment, a satellite controller 31 which controls multiple right ventricular tip electrodes 32a and 32b, multiple right ventricular ring electrodes 34a and 34b, a right ventricular (RV) coil electrode 36, and a superior vena cava (SVC) coil electrode 38. Typically, the right ventricular lead 30 is transvenously inserted into the heart 12 so as to place the right ventricular tip electrode 32b in the right ventricular apex so that the right ventricular coil electrode 36 will be positioned in the right ventricle and the SVC coil electrode 38 will be positioned in the superior vena cava. Accordingly, in this embodiment, the right ventricular satellite controller 31 is capable of controlling delivery of cardiac stimulation in the form of pacing and shock therapy to the right ventricle.

A satellite IC such as satellite controller 31 may control one or more dedicated sensors 37, e.g. MEMS sensors. Various satellite controller and electrode configurations are possible, with satellite controllers controlling one or more electrodes (unipolar or bipolar) and/or sensors. In various embodiments, the satellite IC may be a sensor.

Figure 2:
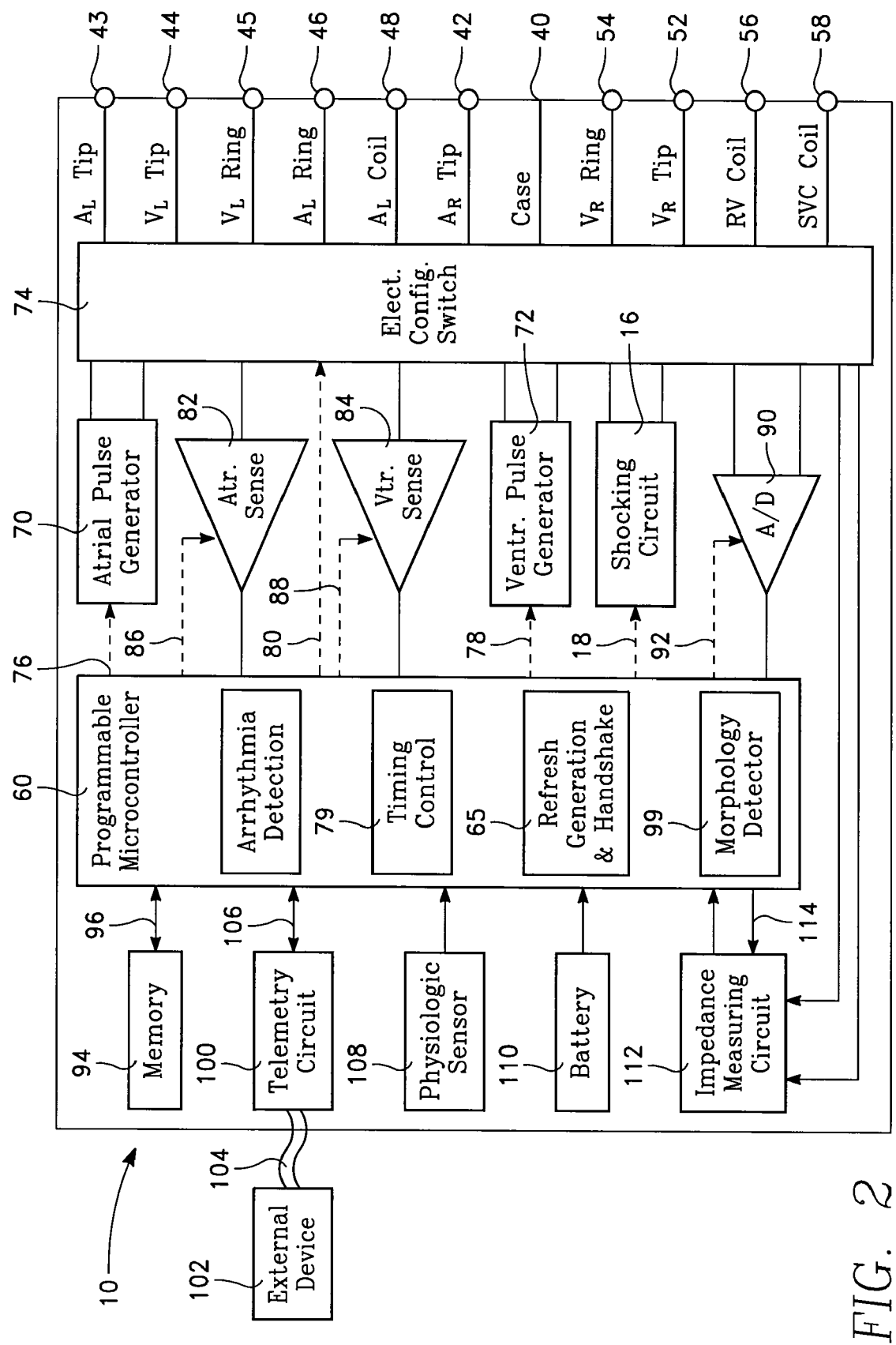
FIG. 2 illustrates a simplified block diagram of the implantable stimulation device.

FIG. 2 illustrates a simplified block diagram of the stimulation device 10. The stimulation device 10 is capable of treating both fast and slow arrhythmias with stimulation therapy, including cardioversion, defibrillation, and pacing stimulation. While a particular stimulation device 10 is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The stimulation device 10 includes a case 40. The case 40 for the stimulation device 10, shown schematically in FIG. 2, is often referred to as the "housing", "can", or "case electrode" and may be programmably selected to act as the return electrode for all "unipolar" modes. The case 40 may further be used as a return electrode individually or in combination with one or more of the coil electrodes, 28, 36 and 38, for shocking purposes. The case 40 further includes a connector (not shown) having a plurality of terminals, 42, 43, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22 and a right atrial ring ($A_R$ RING) terminal 43 adapted for connection to right atrial ring electrode 23. To achieve left chamber sensing, pacing and shocking, the connector can include a left ventricular tip terminal ($V_L$ TIP) 44 and left ventricular ring terminal ($V_L$ RING) 45, a left atrial tip terminal ($A_L$ TIP) 43 and left atrial ring terminal ($A_L$ RING) 46, and a left atrial shocking terminal ($A_L$ COIL) 48, which are adapted for connection to their corresponding electrodes, i.e. the left ventricular tip electrodes 26b and 26d, the left ventricular ring electrodes 26a and 26c, the left atrial tip electrode 27b, the left atrial ring electrode 27a, and the left atrial coil electrode 28, correspondingly. To support right chamber sensing, pacing and shocking, the connector further includes a right ventricular tip terminal ($V_R$ TIP) 52, a right ventricular ring terminal ($V_R$ RING) 54, a right ventricular shocking terminal (RV COIL) 56, and an SVC shocking terminal (SVC COIL) 58, which are adapted for connection to the right ventricular tip electrodes 32a and 32b, the right ventricular ring electrodes 34a and 34b, the right ventricular coil electrode 36, and the SVC coil electrode 38, respectively. The above is an example configuration, other configurations are possible.

At the core of the stimulation device 10 is a programmable microcontroller 60, which controls the various modes of stimulation therapy. As is well known in the art, the microcontroller 60 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator (Vtr. Pulse Generator) 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes a timing control circuit 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

In one embodiment, the stimulation device 10 may include an atrial sensing circuit (Atr. Sense) 82 and a ventricular sensing circuit (Vtr. Sense) 84. The atrial sensing circuit 82 and ventricular sensing circuit 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial sensing circuit 82 and ventricular sensing circuit 84 may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity. Each sensing circuit, 82 and 84, may employ one or more low power, precision amplifiers with programmable gain and/or automatic gain control, bandpass filtering, and a threshold detection circuit, as known in the art, to selectively sense the cardiac signal of interest. The bandpass filtering may include a bandpass filter that passes frequencies between 10 and 70 Hertz (Hz) and rejects frequencies below 10 Hz or above 70 Hz. The automatic gain control enables the stimulation device 10 to deal effectively with the difficult problem of sensing the low amplitude signal characteristics of atrial or ventricular fibrillation. The outputs of the atrial and ventricular sensing circuits 82 and 84 are connected to the microcontroller 60 which, in turn, is able to trigger or inhibit the atrial and ventricular pulse generators, 70 and 72, respectively, in a demand fashion in response to the absence or presence of cardiac activity in the appropriate chambers of the heart.

For arrhythmia detection, the stimulation device 10 may utilize the atrial and ventricular sensing circuits 82 and 84 to sense cardiac signals to determine whether a rhythm is physiologic or pathologic. The timing intervals between sensed events (e.g., P-waves, R-waves, and depolarization events associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks, collectively referred to as "tiered therapy"). Similar capabilities would exist on the atrial channel with respect to tachycardias occurring in the atrium. These would be atrial tachycardias (AT), more rapid atrial tachycardias (Atrial Flutter) and atrial fibrillation (AF).

In another embodiment, the stimulation device 10 may include an analog-to-digital (A/D) data acquisition circuit 90. The data acquisition circuit 90 is configured to acquire an intracardiac signal, convert the raw analog data of the intracardiac signal into a digital signal, and store the digital signals for later processing and/or telemetric transmission to an external device 102. The data acquisition circuit 90 is coupled to the right atrial lead 20, the coronary sinus lead 24, and the right ventricular lead 30 through the switch 74 to sample cardiac signals across any pair of desired electrodes. As shown in FIG. 2 the microcontroller 60 generates a control signal 92 to control operation of the data acquisition circuit 90.

The microcontroller 60 includes an arrhythmia detector 77, which operates to detect an arrhythmia, such as tachycardia and fibrillation, based on the intracardiac signal. The arrhythmia detector 77 senses R-waves in the intracardiac signal, each of which indicates a depolarization event occurring in the heart 12. The arrhythmia detector 77 may sense an R-wave by comparing a voltage amplitude of the intracardiac signal with a voltage threshold value. If the voltage amplitude of the intracardiac signal exceeds the voltage threshold value, the arrhythmia detector 77 senses the R-wave. The arrhythmia detector 77 may also determine an event time for the R-wave occurring at a peak voltage amplitude of the R-wave. The arrhythmia detector 77 may receive an analog intracardiac signal from the sensing circuits 82 and 84 or a digital intracardiac signal from the data acquisition circuit 90. Alternatively, the arrhythmia detector 77 may use the digitized intracardiac signal stored by the data acquisition circuit 90.

The microcontroller 60 may include a morphology detector 99 for confirming R-waves. The morphology detector 99 compares portions of the intracardiac signal with templates of known R-waves to confirm R-waves sensed in the intracardiac signal. In various embodiments, the morphology detector 99 is optional.

In accordance with one embodiment, the microcontroller 60 may include refresh generator 65 which may include optional handshake logic. The microcontroller may generate a refresh waveform signal for delivery it to satellites based on known handshaking protocols. The refresh generator 65 controls refresh circuitry, which may include the atrial and ventricular pulse generators 70 and 72, to provide multi-phasic refresh waveform signals for refreshing the stored power of satellite devices 21, 23, 25, and 31 located within the heart 12 along the leads 20, 24, or/and 30, as discussed in greater detail below. In some embodiments, the refresh generator 65 may be logic or/and circuits located entirely outside of the microcontroller 60.

The microcontroller 60 is further coupled to a memory 94 by a suitable computer bus 96 (e.g., an address and data bus), wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. Other pacing parameters include base rate, rest rate and circadian base rate.

Advantageously, the operating parameters of the stimulation device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller 60 by a control signal 106. The telemetry circuit 100 advantageously allows intracardiac electrograms and status information relating to the operation of the stimulation device 10 (as contained in the microcontroller 60 or memory 94) to be sent to the external device 102 through an established communication link 104.

The stimulation device 10 may further include a physiologic sensor 108, commonly referred to as a "rate-responsive" sensor because it is typically used to adjust pacing stimulation rate according to the exercise state of the patient. However, the physiologic sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses. (V-V delay is typically used only in connection with independently programmable RV and LV leads for biventricular pacing.) While shown as being included within the stimulation device 10, it is to be understood that the physiologic sensor 108 may also be external to the stimulation device 10, yet still be implanted within or carried by the patient, such as satellite sensor 37. A common type of rate responsive sensor is an activity sensor, such as an accelerometer or a piezoelectric crystal, which is mounted within the case 40 of the stimulation device 10. Other types of physiologic sensors are also known, for example, sensors that sense the oxygen content of blood, respiration rate and/or minute ventilation, pH of blood, ventricular gradient, etc. However, any sensor may be used which is capable of sensing a physiological parameter that corresponds to the exercise state of the patient. In some embodiments, the satellite sensor 37 may be powered independently and thus require refresh charging.

The stimulation device additionally includes a battery 110, which provides operating power to all of the circuits shown in FIG. 2. For the stimulation device 10, which employs shocking therapy, the battery 110 should be capable of operating at low current drains for long periods of time, and then be capable of providing high-current pulses (for capacitor charging) when the patient requires a shock pulse. The battery 110 should also have a predictable discharge characteristic so that elective replacement time can be detected. Accordingly, the stimulation device 10 may employ lithium/silver vanadium oxide batteries. As further shown in FIG. 2, the stimulation device 10 is shown as having a measuring circuit 112 which is enabled by the microcontroller 60 via a control signal 114.

In the case where the stimulation device 10 is intended to operate as an implantable cardioverter/defibrillator (ICD) device, the stimulation device 10 detects and confirms the occurrence of an arrhythmia, and automatically applies an appropriate antitachycardia pacing therapy or electrical shock therapy to the heart 12 for terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the right ventricular coil electrode 36, and/or the SVC coil electrode 38. As noted above, the case 40 may act as an active electrode in combination with the right ventricular coil electrode 36, or as part of a split electrical vector using the SVC coil electrode 38 or the left atrial coil electrode 28 (i.e., using the right ventricular coil electrode as a common electrode).

Cardioversion shocks are of relatively low to moderate energy level (so as to minimize the current drain on the battery) and are usually between 5 to 20 joules. Typically, cardioversion shocks are synchronized with an R-wave. Defibrillation shocks are generally of moderate to high energy level (i.e., corresponding to thresholds in the range of 5 to 40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Satellite Devices and Refresh

Satellite devices are powered and require refresh charging for continued operation. The voltage-balanced feature inhibits build-up of non-zero-mean voltages at the electrode interface, voltages that are detrimental to accurate electrogram sensing and to ECG acquisition.

Figure 3A:
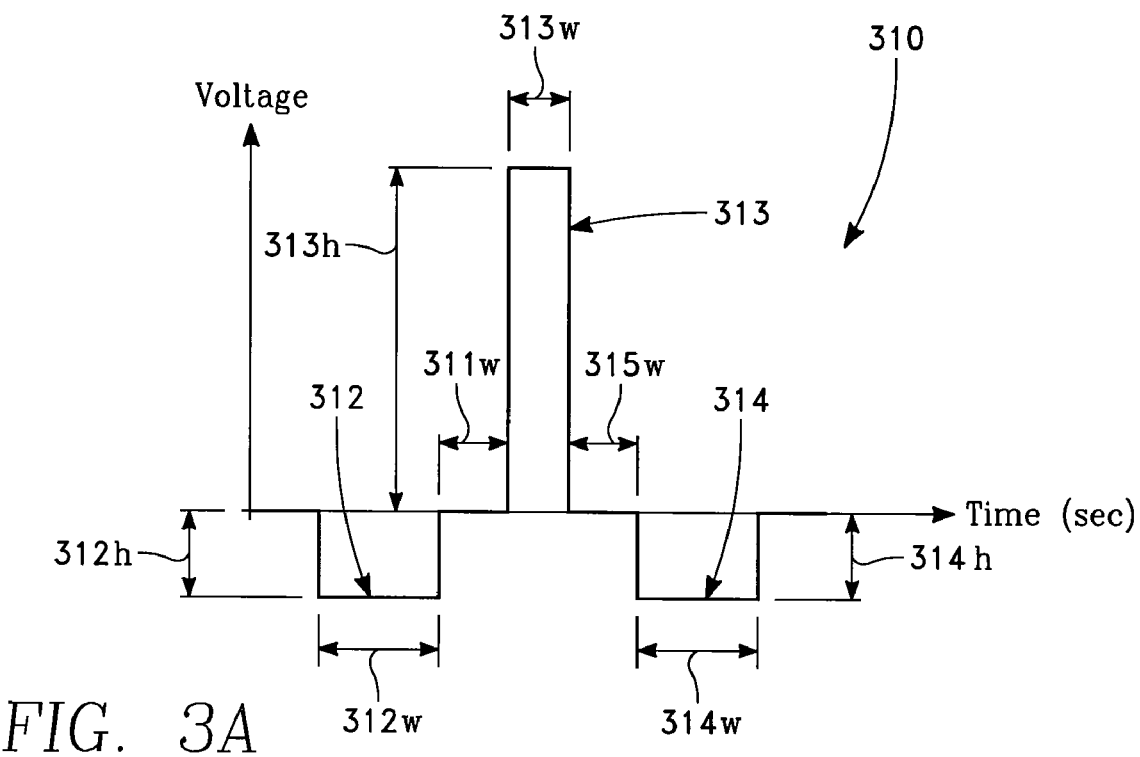
FIGS. 3A and 3B are plots of voltage versus time of some examples of balanced tri-phasic pulse waveforms.
Figure 3B:
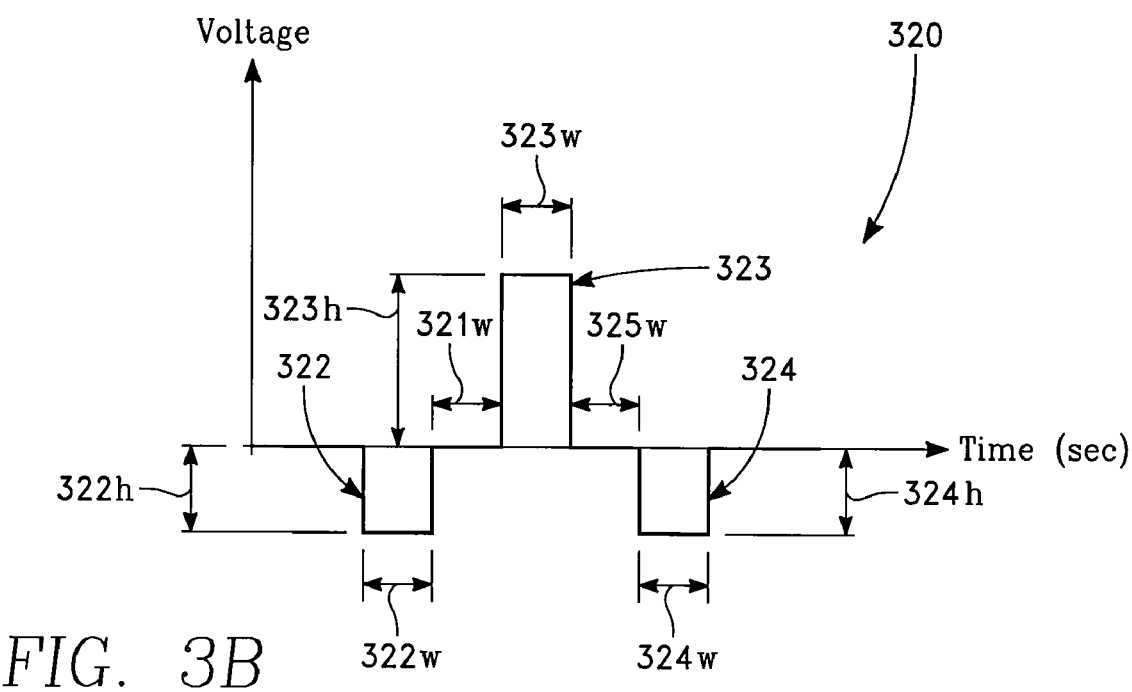

FIGS. 3A and 3B are plots of voltage versus time of some examples of balanced tri-phasic pulse waveform signals. The balanced tri-phasic pulse waveform signals may be a tri-phasic pulse waveform signal 310 with unequal duration phase components, or/and a tri-phasic pulse waveform signal 320 with equal duration phase components, as shown in the examples of FIGS. 3A and 3B, respectively. The waveform signal 310 with unequal durations for the positive and negative components may be referred to as an asymmetric duration waveform signal, and the waveform signal 320 with equal durations for the positive and negative components may be referred to as a symmetrical duration waveform signal.

In one embodiment, the refresh voltage waveform signal may consist of multiple phases, the first and the last phases having a longer duration than the intermediary phases. In the asymmetric duration tri-phasic waveform signal 310 shown in FIG. 3A, the pulse widths of the surrounding negative components 312 and 314 do not have the same pulse width of the central positive component 313. In the tri-phasic waveform signal 310, the pulse widths 312$w$ and 314$w$ of the negative components 312 and 314 are twice the width 313$w$ of the positive central component 313. The positive central component 313 is separated from the negative component 312 by a null period having a duration 311$w$ equal to the pulse width 313$w$ of the central component 313, and is also separated from the negative component 314 by a null period having a duration 315$w$ equal to the pulse width 313$w$ of the central component 313. The amplitude 313$h$ of the positive component 313 is four times the amplitude 312$h$ or 314$h$ of the negative component 312 or 314, so that the energy in the positive component 313 balances the combined energy in the negative components 312 and 314. For example, the amplitude of the positive central component 313 may be 10 Volts and the amplitudes of the negative components 312 and 314 may be 2½ Volts.

In the symmetric duration tri-phasic waveform signal 320 of FIG. 3B, the pulse widths of the surrounding negative components 322 and 324 have the same as the pulse width as the central positive component 323. In the tri-phasic waveform signal 320, the pulse widths 322$w$ and 324$w$ of the negative components 322 and 324 are the same as the width 323$w$ of the positive central component 323. The positive central component 323 is separated from the negative component 322 by a null period having a duration 321$w$ equal to the pulse width 323$w$ of the central component 323, and is also separated from the negative component 324 by a null period having a duration 325$w$ equal to the pulse width 323$w$ of the central component 323. The amplitude 323$h$ of the positive component 323 is two times the amplitude 322$h$ or 324$h$ of the negative component 322 or 324, so that the energy in the positive component 323 balances the combined energy in the negative components 322 and 324. In these examples, the overall duration of the waveform signal 310 is the sum of the durations of 322$w$, 321$w$, 323$w$, 325$w$, and 324$w$. For example, the amplitude of the positive central component 323 may be 5 Volts and the amplitude of the negative components 322 and 324 may be 2½ Volts.

The duration of the null periods 311$w$, 315$w$, 321$w$, and 325$w$ may vary. The null periods 311$w$, 315$w$, 321$w$, and 325$w$ allow sufficient time for the circuitry to transition from negative to positive or positive to negative, as applicable. In some implementations, null periods are not required. Thus, the null periods may be from 0 up to about 10 microseconds, for example, depending on the size of the electrode, etc.

The refresh signal may be used primarily to charge the capacitor, but, it could also be modulated to configure the electrodes, or other satellite device. It is possible in some embodiments to modulate the tri-phasic pulse refresh signal to convey information to the satellite device. The modulation could be used for example, to configure the electrodes so that some electrodes are used for defibrillation, some electrodes for pacing, and some for sensing. The modulation may be amplitude modulation, frequency modulation, pulse position modulation, pulse width modulation, null period modulation, etc. Thus, in one embodiment for example, the amplitude of the voltage of the one or more of the components may be modulated to contain information instructing the satellite integrated circuits which one is to receive the energy of the tri-phasic refresh signals.

The tri-phasic waveform may be modulated with any type of configuration information, status information, or the like. For example, in the case of a satellite pacemaker, the configuration may include when and how to apply pacing pulses. Other configuration information such as pacing or defibrillation parameters, electrode configuration, etc. may be supplied to the satellite device. Similarly, status information such as pacing impedance, shock impedance, supply voltage level, active electrode, etc. may be supplied.

An advantage of a tri-phasic waveform signal is that it can have a broader frequency spectrum, such as by using pulse width modulation. Thus, it provides flexibility to modulate for communication purposes.

Figure 4A:
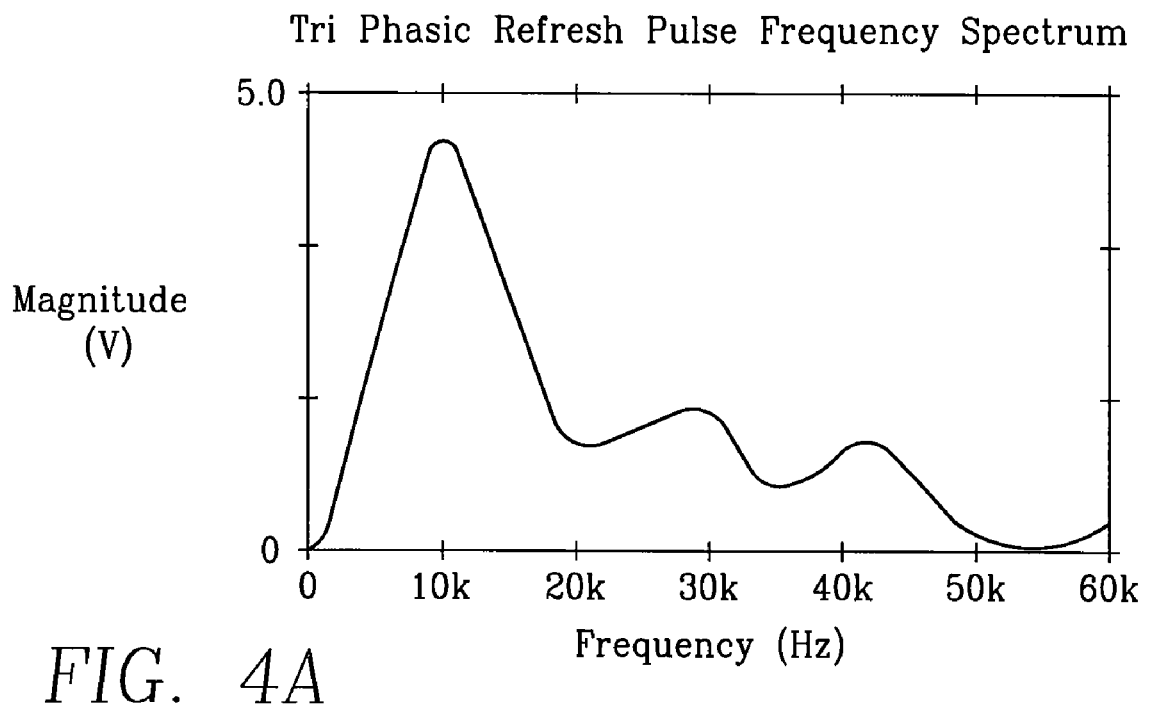
FIG. 4A shows a plot of an example frequency spectrum of a tri-phasic refresh signal.
Figure 4B:
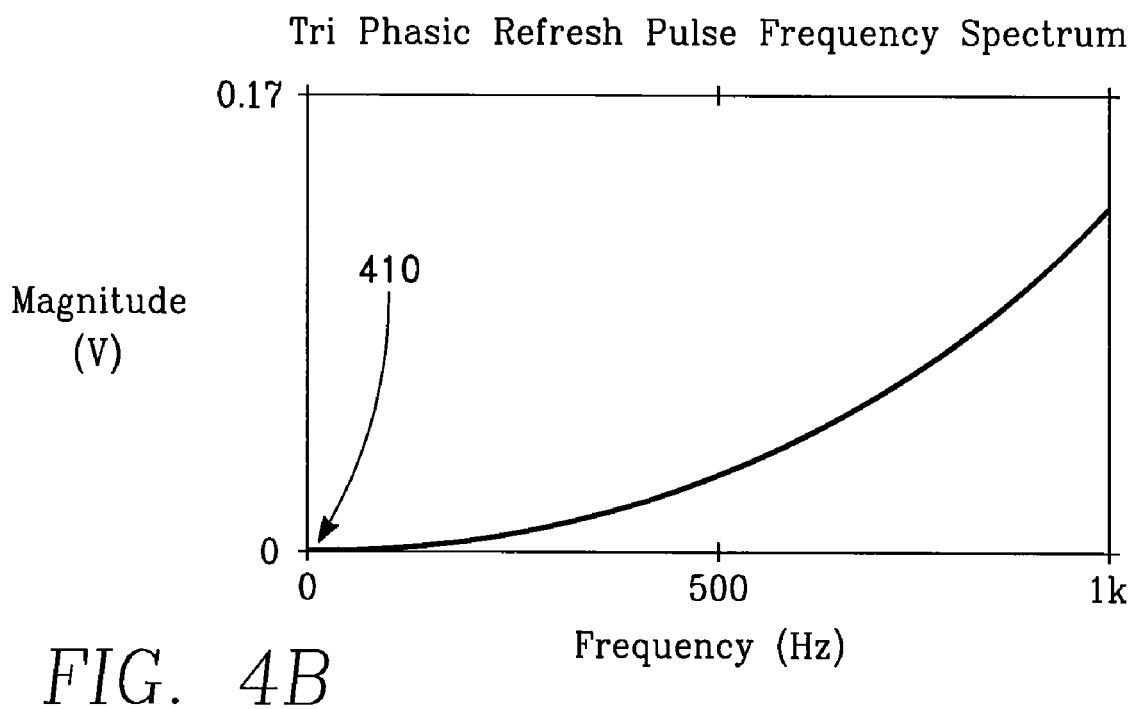
FIG. 4B shows a plot of an example frequency spectrum of FIG. 4A near the sensing frequency.

FIG. 4A shows a plot of an example frequency spectrum of a tri-phasic refresh signal of FIG. 3A. The plot indicates that the high-frequency components can be filtered by electrogram processing systems (e.g. EGM acquisition blocks inside the ICD or EP recording systems). FIG. 4B shows a plot of the example frequency spectrum of FIG. 4A near the sensing frequency 410. The plot illustrates that there is no DC components at the sensing frequency range of about 10-120 Hz.

Figure 5:
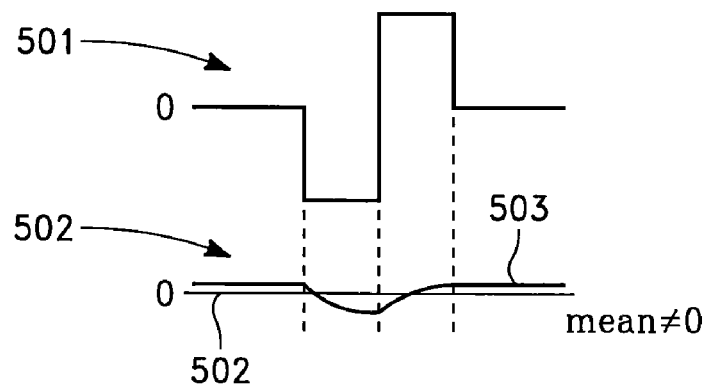
Figure 6:
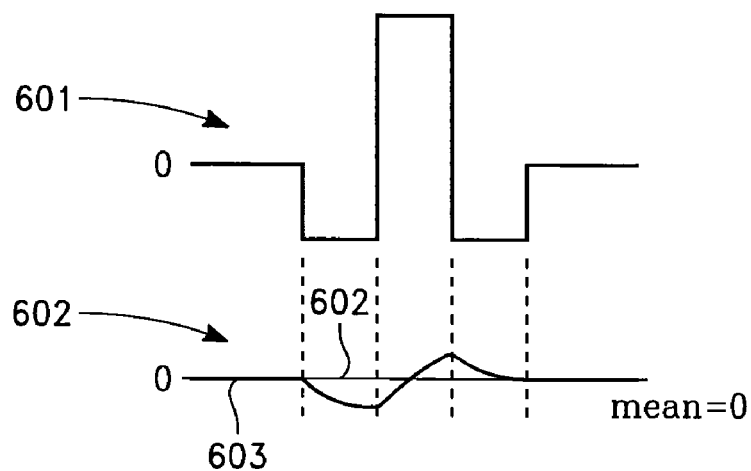

Turning to FIGS. 5 and 6, the tri-phasic waveform signal is charge balanced and voltage balanced, so that when passing through a capacitor, the voltage that builds on the capacitor in the path would have a net voltage of zero. This is important because some capacitors are used in a sensing circuit. If there is some residual voltage built up on the capacitors, the residual charge can affect the electrograms or other sense signals. In various embodiments, however, the waveform signal passing through a capacitor has a mean voltage value of zero.

FIG. 5 is a plot of a regular negative-positive square wave 501 and a corresponding plot 502 illustrating the voltage of a capacitor 503 as the regular negative-positive square wave 501 passes through. When the regular negative-positive square wave 501 passes through the capacitor, the mean capacitor voltage 502 of the capacitor is not zero as shown in FIG. 5.

FIG. 6 shows a plot of a tri-phasic voltage waveform signal 601 and a corresponding plot 602 illustrating the voltage of a capacitor 603 as tri-phasic voltage waveform signal 601 passes through. The waveform signal 601 is voltage balanced which means that as the waveform signal 601 passes through a capacitor, the mean capacitor voltage 602 of the capacitor is zero, as is any coupled voltage into any associated internal or external electrogram sensing circuit, as shown in FIG. 6.

Although shown as balanced tri-phasic voltage waveforms, balanced tri-phasic current waveforms may be used that cause a net zero mean voltage on the capacitor. In the case of a current waveform (not shown), a typical range of amplitudes may be in about the 5-10 milliamp range, with a duration less than the time constant of the electrode/electrolyte interface, 1 millisecond, for example. In either case, the time constant, and thus the values, will vary based on the dimensions of the electrodes.

An advantage of the tri-phasic waveform signal is that since the voltage has a zero mean value, the disruption to the electrode/electrolyte(blood) interface will be minimal. Normally, there is a possibility of building up an electrochemical potential at the electrode/electrolyte interface. Having a zero mean value of the waveform signal reduces this effect.

Figure 7:
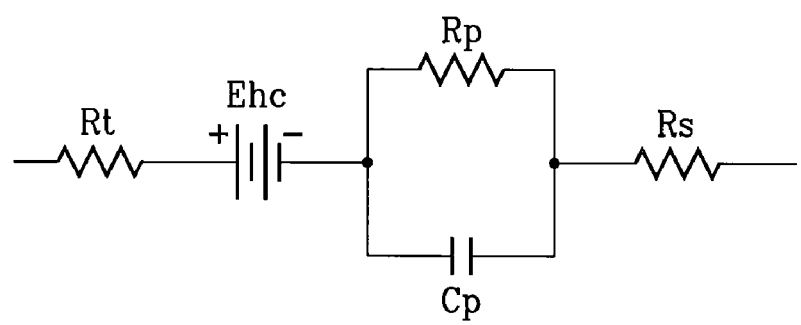
FIG. 7 shows an equivalent circuit including the electrode electrolyte interface.

FIG. 7 shows an electrode-electrolyte equivalent circuit including the electrode/electrolyte interface, where $R_t$ is the tissue resistance, $R_p$ is the polarization resistance, $C_p$ is the polarization capacitance, and $R_s$ is the series resistance of the electrode. $R_p$ and $C_p$ are the parallel resistor and capacitor that model the interface. $E_{hc}$ is the half-cell voltage. If the overall duration of the balanced tri-phasic waveform signal is kept less than the time constant of the electrode-electrolyte circuit, for example 0.1 to 4 or 5 milliseconds, it can just pass through "unobserved" by the chemical reaction that could develop at the electrode/electrolyte interface. In some embodiments, because it is not going to disturb the electrode/electrolyte interface there does not need to be an open circuited inside the satellite integrated circuit when refresh occurs.

The capacitive time constant θ for the eletrode-electrolyte equivalent circuit is approximately given by:

$$\theta \cdot C_p * R_p * (R_s + R_t)$$  Equation 1

Typical values for $R_p$ and $C_p$ are in the range from 200 to 2000 ohms and 0.5 to 5 microfarads, respectively. Thus, the equivalent typical time constants can be in the range from 0.1 to 10 milliseconds. The exact values depend on size of the electrode, material, and electrolyte type. Similarly, $E_{hc}$ can be as high as 0.7 volts. It is important to note that the charge- and voltage-balanced feature of the refresh waveform signal minimizes disturbance produced to the electrode/electrolyte interface. Therefore, it also minimizes distortions to EGM signals. The duration of these waveform signals should be shorter, or comparable to the time constants of the electrode-electrolyte circuit. Thus, in some embodiments, the duration of the waveform signal may be in a range from about 0.1 to about 10 milliseconds. In some embodiments, the duration of the waveform signal may be in a range from about 0.1 to about 5 milliseconds. In some embodiments, the duration of the waveform signal may be less than about 4 milliseconds. Consequently, if the waveform signals have a duration shorter than, or comparable to the time constant of the electrode-electrolyte circuit, they can have a less disturbing effect on the polarization potentials seen at the interface. Thus, the artifacts may be minimized.

Figure 8:
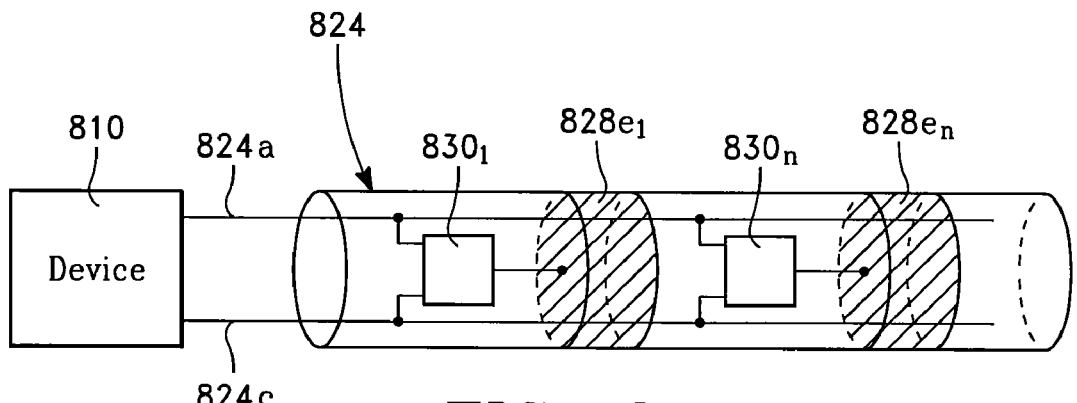
FIG. 8 shows a simplified schematic of a possible embodiment of an implantable cardiac device.

FIG. 8 shows a simplified schematic of a possible ICD in accordance with one embodiment. Extending from the stimulation device housing 810 is a lead 824 having multiple electrodes $828e_1$ and $828e_n$. Multiple satellite controllers $830_1$ and $830_n$ detect the tri-phasic waveform signals and refresh their stored charge with energy from the tri-phasic waveform signal transmit along the anode and/or cathode conductors 824a and/or 824c. There may be any number n of electrodes 828n space along the lead 824. The satellite IC controllers $830e_1$ and $830e_n$ may determine which satellite controller $830e_1$ and/or $830e_n$ is refreshed by the tri-phasic waveform signal. They may determine this with internal logic and charge detection, or based on information supplied to them, which may be supplied along with, or by, the tri-phasic waveform signal.

Figure 9:
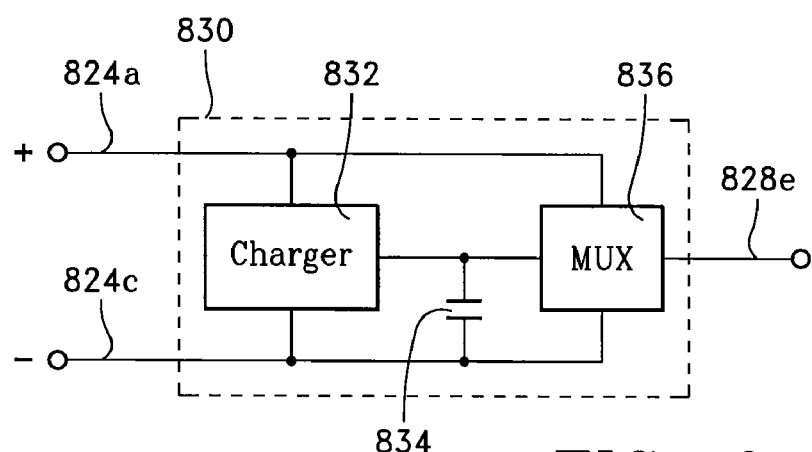
FIG. 9 shows a simplified block diagram of a possible embodiment of a satellite controller.

FIG. 9 shows a simplified block diagram of a possible satellite controller 830 in accordance with one embodiment. The anode and cathode conductors 824a and 824c are connected via an internal controller 836 to the electrode 828e. In some embodiments, the internal controller 830 may be a multiplexer device. A charger 832 extracts the energy from the refresh signal and provides it to the capacitor 834 or other charge storage device.

In some embodiments, because the tri-phasic waveform signal is so short and is voltage mean zero, the microprocessor circuitry inside the ICD does not have to be disconnected from the waveform generator, as would be necessary for a standard negative-positive square wave waveform.

Thus, in some embodiments, the refresh voltage waveform signal is provided which will not disturb or affect the sensing operation. This allows the sensing system to operate continuously without any black-out period. This refresh waveform signal can be delivered at any time and any rate, either stone-alone or right after the pacing pulse.

Figure 10:
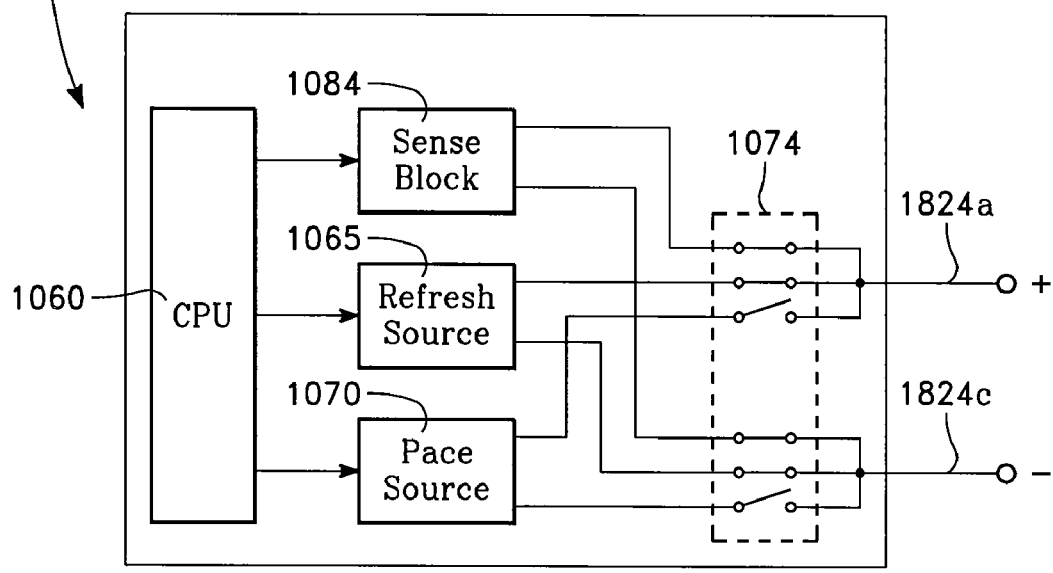
FIG. 10 shows a simplified block diagram of a possible embodiment of an implantable stimulation device.

FIG. 10 shows a simplified block diagram of an implantable stimulation device 1010 in accordance with an embodiment. As shown, the sense circuit 1084 may be connected to the anode and cathode conductors 1024a and 1024c while the refresh source 1065 is connected to the anode and cathode conductors 1024a and 1024c and is providing the tri-phasic refresh waveform signal. The refresh source 1065 may be connected to the microcontroller 1060 without a switch, if desired. The refresh source 1065 may deliver the tri-phasic refresh waveform signal without timing it to coincide with the pace source 1070 delivery of a pacing pulse.

With a regular negative-positive square wave waveform 501 (shown in FIG. 5), the switch block 1074 would open circuit the sense circuit 1084 from the anode and cathode conductors 1024a and 1024c when the refresh source switch is close circuited and the refresh source is sending the regular negative-positive square wave waveform 501 of FIG. 5.

In various embodiments, the unique multi-phasic voltage waveform signal has a zero amplitude component at the DC and the low frequency region. The regular sensing system has a band-pass frequency response between DC and hundreds of Hz. Therefore, this waveform signal is transparent and will not be detected by the sensing system. As such, in various embodiments, the sensing system can be operated continuously regardless of the presence of the refresh signals.

Although discussed with reference to a tri-phasic waveform signal, the waveform signal may be multi-phasic, for example penta-phasic, or other multi-phasic waveform signal. Various embodiments generate a satellite refresh current or voltage signal with a waveform that is: charge and voltage balanced, multiphasic, with a total duration less than the charging time constant of the electrode-electrolyte interface, with equal or unequal positive/negative phase durations, decreasing phase amplitudes, alternating phase signs, and with null durations in between phases. In one embodiment, the refresh signal has a voltage waveform with five phases. As discussed above with reference to FIG. 3A, in one embodiment, the refresh signal has three, phases, with the first and the last phases having a longer duration than the intermediary phase. In some embodiments, the waveform signal approximates sin(x)/x, thereby has a wide and quasi-flat frequency spectrum. Other implementations of are possible.

The voltage-balanced feature inhibits build-up of non-zero-mean voltages at the electrode interface. Such voltages are detrimental to accurate electrogram sensing and to ECG acquisition. The null periods in between phases provide the required time for rectifying the signal to provide the charge to the satellite internal voltage charger 832 (FIG. 9). Rectification can be achieved with a full-bridge rectifier (not shown in FIG. 9) that can be implemented in either bipolar (e.g. diodes) or CMOS (e.g. FETs) processes using known techniques.

In some embodiments, the width or amplitude, or both, of the multi-phasic waveform signal could be modulated by known techniques, to send or receive additional configuration or status information to the satellites $830_1$, and $830_n$.

In some embodiments (not show), there may be a central negative component with surrounding positive components (not shown). Moreover, the waveform signal need not be symmetrical about a central axis through the central component of the waveform signal as is the case in the example waveform signals 310 and 320 of FIGS. 3A and 3B.

In some embodiments, the power to the satellite may be supplied via a wire system as discussed above. In other embodiments, the balanced multi-phasic refresh waveform signal may supply power via a wireless system. Although referred to as a refresh signal, it is not limited to refresh charging and is intended to include all types of charging.

Although exemplary methods, devices, systems, etc., have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

What is claimed is:

1. An implantable cardiac device comprising:
   a) an implantable stimulation device;
   b) an implantable satellite device electrically coupled to the implantable stimulation device and comprising a charge storage device; and
   c) the implantable stimulation device comprising a refresh generator configured to generate a charge and voltage balanced multi-phasic refresh signal having a duration less than a capacitive time constant of an electrode-electrolyte interface of the implantable cardiac device and transmit the charge and voltage balanced multi-phasic signal to the implantable satellite device for charging the charge storage device.

2. The device of claim 1, wherein the refresh generator is configured to generate a tri-phasic refresh signal.

3. The device of claim 1, wherein the refresh generator is configured to generate a charge and voltage balanced multi-phasic refresh signal having alternating phase signs and null durations between the alternating phases.

4. The device of claim 1, wherein the refresh generator is configured to generate a charge and voltage balanced tri-phasic refresh signal having a positive voltage component having a duration and two negative voltage components such that the positive voltage component and each of the two negative voltage components have a same duration.

5. The device of claim 4, wherein the refresh generator is configured to generate a charge and voltage balanced tri-phasic refresh signal having a null duration between each of the two negative voltage components and the positive voltage component, and wherein the null durations have the same duration as the positive voltage component and each of the two negative voltage components.

6. The device of claim 1, wherein the refresh generator is configured to generate a charge and voltage balanced tri-phasic refresh signal having a positive voltage component and two negative voltage components such that the positive voltage component has a different duration than each of the two negative voltage components.

7. The device of claim 6, wherein the refresh generator is configured to generate a charge and voltage balanced tri-phasic refresh signal having a null duration between each of the two negative voltage components and the positive voltage component.

8. The device of claim 1, wherein the refresh generator is configured to generate a charge and voltage balanced multi-phasic refresh signal having a duration less than a polarization capacitance of the electrode/electrolyte interface times a polarization resistance in parallel with a sum of an electrode circuit series resistance and a tissue resistance.

9. The device of claim 1, wherein the refresh generator is configured to generate a charge and voltage balanced multi-phasic refresh signal having a duration between about 0.1 milliseconds and 10 milliseconds.

10. The device of claim 1, wherein the refresh generator is configured to generate a charge and voltage balanced multi-phasic refresh signal having a duration between about 0.1 milliseconds and 6 milliseconds.

11. The device of claim 1, wherein the refresh generator is configured to modulate the multi-phasic waveform refresh signal.

12. The device of claim 1, wherein the refresh generator is configured to modulate the multi-phasic waveform refresh signal with at least one of: (a) configuration information; or (b) status information.

13. The device of claim 1, wherein the refresh generator is configured to modulate the multi-phasic waveform refresh signal using pulse width modulation.

14. The device of claim 1, wherein the refresh generator is configured to modulate the multi-phasic waveform refresh signal using amplitude modulation.

15. The device of claim 1, wherein the implantable cardiac device is capable of performing continuous physiologic signal sensing before, during, and after refresh charging without black-out intervals.

16. The device of claim 1, wherein the satellite device comprises at least one of: (a) a controller; (b) a sensor; or (c) a satellite pacemaker.

17. The device of claim 1, wherein the implantable satellite device is coupled to the implantable stimulation device via a lead, and further comprising at least one electrode connected to via the lead to the implantable satellite device.

18. The device of claim 17, further comprising a plurality of implantable satellite devices and a plurality of electrodes connected along the lead, and wherein the plurality of satellite devices comprise satellite controllers.

19. An implantable cardiac device comprising:
  a) an implantable stimulation device connected via a lead to a satellite controller and an electrode;
  b) the satellite controller comprising a charge storage device;
  c) the implantable stimulation device comprising a refresh generator configured to generate a charge and voltage balanced multi-phasic refresh signal for transmission along the lead to charge the charge storage device;
  d) the refresh generator being configured to generate the charge and voltage balanced multi-phasic waveform refresh signal having alternating phase signs and null durations between the alternating phases; and
  e) the refresh generator being configured to generate the charge and voltage balanced multi-phasic waveform refresh signal having a duration less than a capacitive time constant of an electrode/electrolyte interface of the implantable cardiac device.

20. The device of claim 19, further comprises a plurality of implantable satellite controllers and a plurality of electrodes connected along the lead.

21. The device of claim 19, wherein the refresh generator is configured to modulate the multi-phasic waveform refresh signal.

22. The device of claim 19, wherein the implantable cardiac device is capable of performing continuous physiologic signal sensing before, during, and after refresh charging without black-out intervals.

23. A method in an implantable cardiac device for charging a satellite device, the method comprising supplying to the satellite device a charge and voltage balanced multi-phasic waveform refresh signal having a duration less than a capacitive time constant of an electrode-electrolyte interface of the implantable cardiac device.

24. The method of claim 23, wherein supplying the charge and voltage balanced multi-phasic waveform refresh signal comprises supplying the charge and voltage balanced multi-phasic waveform refresh signal having a duration less than a polarization capacitance of the electrode/electrolyte interface times a polarization resistance in parallel with a sum of an electrode circuit series resistance and a tissue resistance.

25. The method of claim 23, wherein supplying the charge and voltage balanced multi-phasic waveform refresh signal comprises supplying the charge and voltage balanced multi-phasic waveform refresh signal having a duration between about 0.1 milliseconds and 10 milliseconds.

26. The method of claim 23, wherein supplying the charge and voltage balanced multi-phasic waveform refresh signal comprises supplying the charge and voltage balanced multi-phasic waveform refresh signal having a duration between about 0.1 milliseconds and 5 milliseconds.

27. The method of claim 23, wherein supplying the charge and voltage balanced multi-phasic waveform refresh signal comprises supplying a charge and voltage balanced waveform refresh signal having at least on positive voltage component having a duration and at least two negative voltage components each having a duration such that the at least one positive voltage component and each of the at least two negative voltage components have a same duration.

28. The method of claim 23, wherein supplying the charge and voltage balanced multi-phasic waveform refresh signal comprises supplying a charge and voltage balanced waveform refresh signal having at least on positive voltage component having a duration and at least two negative voltage components each having a duration such that the at least one positive voltage component has a different duration than each of the at least two negative voltage components.

29. The method of claim 23, wherein supplying the charge and voltage balanced multi-phasic waveform refresh signal comprises supplying the charge and voltage balanced multi-phasic waveform refresh signal to a satellite device comprising at least one of: (a) a controller; or (b) a sensor.

30. The method of claim 23, wherein supplying the supplying the charge and voltage balanced multi-phasic waveform refresh signal further comprises modulating the multi-phasic waveform refresh signal.

31. The method of claim 30, wherein modulating the multi-phasic waveform refresh signal comprises communicating at least one of: (a) configuration information; or (b) status information.

32. The method of claim 30, wherein modulating the multi-phasic waveform refresh signal comprises pulse width modulation.

33. The method of claim 30, wherein modulating the multi-phasic waveform refresh signal comprises amplitude modulation.

34. The method of claim 23, wherein supplying the charge and voltage balanced multi-phasic waveform refresh signal comprises supplying tri-phasic charge and voltage balanced waveform refresh signal.

35. The method of claim 23, further comprising performing continuous physiologic signal sensing before, during, and after refresh charging without black-out intervals.

36. The method of claim 23, wherein supplying the charge balanced multi-phasic waveform comprises supplying a voltage signal.

37. The method of claim 23, wherein supplying the charge balanced multi-phasic waveform comprises supplying a current signal.

* * * * *